United States Patent [19]

Enami et al.

[11] Patent Number: 5,153,332

[45] Date of Patent: Oct. 6, 1992

[54] ORGANOCYCLOSILOXANE AND METHOD FOR ITS PREPARATION

[75] Inventors: Hiroji Enami; Shoji Akamatsu, both of Ichihara, Japan

[73] Assignee: Dow Corning Toray Silicone Company, Ltd., Tokyo, Japan

[21] Appl. No.: 757,362

[22] Filed: Sep. 10, 1991

[30] Foreign Application Priority Data

Sep. 13, 1990 [JP]  Japan ................................ 2-242893

[51] Int. Cl.$^5$ .......................... C07F 7/08; C07F 7/10; C07F 7/18
[52] U.S. Cl. .................................... 549/215; 556/410; 556/434; 556/440; 556/449; 556/457
[58] Field of Search ............... 556/434, 410, 449, 457, 556/440; 549/215

[56] References Cited

U.S. PATENT DOCUMENTS

| | | | |
|---|---|---|---|
| 3,452,071 | 6/1969 | Sporch | 556/436 |
| 3,452,072 | 6/1969 | Sporch | 556/436 X |
| 3,560,435 | 2/1971 | See | 556/434 X |
| 4,461,867 | 7/1984 | Surprenant | 524/788 |
| 4,587,354 | 5/1986 | Takago et al. | 556/417 |

FOREIGN PATENT DOCUMENTS 8807536 10/1988 World Int. Prop. O. .

Primary Examiner—Paul F. Shaver
Attorney, Agent, or Firm—Alexander Weitz

[57] ABSTRACT

An organocyclosiloxane is disclosed which has both silicon-bonded alkoxy groups and organofunctional groups within each molecule. This cyclic siloxane finds utility as a coupling agent and has the general formula

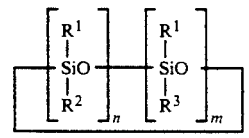

wherein $R^1$ is independently selected from the group consisting of a monovalent hydrocarbon group having 1 to 8 carbon atoms and a monovalent halogen-substituted hydrocarbon group having 1 to 8 carbon atoms, $R^2$ is selected from the group consisting of an alkoxy group and an alkoxysilylalkyl group, $R^3$ is an organofunctional group selected from the group consisting of glycidoxyalkyl groups, methacryloxyalkyl groups, N-(trialkylsilyl)aminoalkyl groups, (hydroxyphenyl)alkyl groups, and haloalkyl groups and n and m each represent an integer having a value of 1 to 6 with the proviso that $n+m$ is an integer with a value of 3 to 8.

7 Claims, No Drawings

ORGANOCYCLOSILOXANE AND METHOD FOR ITS PREPARATION

FIELD OF THE INVENTION

The present invention relates to a novel organocyclosiloxane, and, more particularly, relates to an organocyclosiloxane which contains both silicon-bonded alkoxy and organofunctional groups in each molecule.

BACKGROUND OF THE INVENTION

Various types of organofunctional group-containing organocyclosiloxanes are already known. For example, reference is made to the azide-containing cyclic polyorganosiloxane disclosed in Japanese Patent Application Laid Open [Kokai or Unexamined] Number 54-30300 [30,300/79], the cyclosiloxane derivative disclosed in Japanese Patent Application Laid Open Number 60-163887 [163,887/85], and the difunctional organocyclosiloxane disclosed in Japanese Patent Publication Number 63-18977 [18,977/88].

With regard to organocyclosiloxane which contains the silicon-bonded alkoxy group, reference is made to the disilyl-bridged compound disclosed in Japanese Patent Application Laid Open Number 64-6036 [6,036/89].

However, organocyclosiloxane which contains both silicon-bonded alkoxy and organofunctional groups within each molecule has remained unknown.

SUMMARY OF THE INVENTION

The present inventors carried out extensive investigations with regard to organocyclosiloxane which would contain both silicon-bonded alkoxy and organofunctional groups within each molecule, and the present invention was developed as a result.

Thus, the present invention takes as its object the introduction of organocyclosiloxane which contains both silicon-bonded alkoxy and organofunctional groups within each molecule, which is a novel compound, as well as the introduction of a method for its preparation. The organocyclosiloxane of the present invention is therefore represented by the general formula

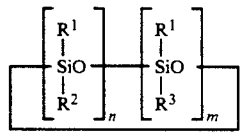

wherein $R^1$ is independently selected from the group consisting of a monovalent hydrocarbon group having 1 to 8 carbon atoms and a monovalent halogen-substituted hydrocarbon group having 1 to 8 carbon atoms, $R^2$ is selected from the group consisting of an alkoxy group and an alkoxysilylalkyl group, $R^3$ is an organofunctional group selected from the group consisting of glycidoxyalkyl groups, methacryloxyalkyl groups, N-(trialkylsilyl)aminoalkyl groups, (hydroxyphenyl)alkyl groups, and haloalkyl groups and n and m each represent an integer having a value of 1 to 6 with the proviso that n+m is an integer with a value of 3 to 8.

DETAILED DESCRIPTION OF THE INVENTION

The group $R^1$ in the preceding formula is a monovalent hydrocarbon group or halogen-substituted hydrocarbon group, having 1 to 8 carbon atoms. This group is concretely exemplified by alkyl groups, such as methyl, ethyl, propyl, and butyl; aryl groups, such as phenyl and tolyl; and substituted alkyl groups, such as chloromethyl and 3,3,3-trifluoropropyl. A range of 1 to 8 is specified for the number of carbons in $R^1$ because the industrial production of the organocyclosiloxane becomes highly problematic when $R^1$ contains more than 8 carbons. $R^1$ is preferably methyl.

The group $R^2$ in the preceding formula comprises an alkoxy group as exemplified by methoxy and ethoxy or an (alkoxysilyl)alkyl group as exemplified by (trimethoxysilyl)ethyl, (trimethoxysilyl)propyl, (methyldimethoxysilyl)ethyl, (triethoxysilyl)ethyl, (triethoxysilyl)propyl, and (diethoxymethylsilyl)ethyl. $R^2$ is an essential functional group moiety in the organocyclosiloxane according to the present invention, and it is this group which gives the organocyclosiloxane according to the present invention a characteristic and excellent reactivity for inorganics when this organocyclosiloxane is used as a silane coupling agent.

The group $R^3$ in the preceding formula comprises an organic group selected from glycidoxyalkyl groups, methacryloxyalkyl groups, N-(trialkylsilyl)aminoalkyl groups, (hydroxyphenyl)alkyl groups, and haloalkyl groups. Concrete examples in this regard are glycidoxyethyl and glycidoxypropyl for the glycidoxyalkyl groups; methacryloxyethyl and methacryloxypropyl for the methacryloxyalkyl groups; N-(trimethylsilyl)aminopropyl and N-(triethylsilyl)aminopropyl for the N-(trialkylsilyl)aminoalkyl groups; o-(hydroxyphenyl)propyl, m-(hydroxyphenyl)propyl, and p-(hydroxyphenyl)propyl for the (hydroxyphenyl)alkyl groups; and chloropropyl and chlorobutyl for the haloalkyl groups. The organocyclosiloxane according to the present invention may contain more than one type of the aforementioned organic groups. Like $R^2$, the group $R^3$ is an essential functional group moiety, and it is this group which provides the organocyclosiloxane according to the present invention with a characteristic and excellent reactivity with and affinity for organic resin when this organocyclosiloxane is added to organic resin.

In the preceding formula, n and m, respectively represent the number of $R^2$-containing siloxane units and the number of $R^3$-containing siloxane units within the single molecule of the organocyclosiloxane according to the present invention, n and m each being integers in the range of 1 to 6, and the sum of n plus m being an integer in the range of 3 to 8. The organocyclosiloxane does not exist for a sum of n+m of less than 3, while synthesis of the organocyclosiloxane becomes problematic when the sum of n+m exceeds 8.

Examples of organocyclosiloxane according to the present invention are provided below.

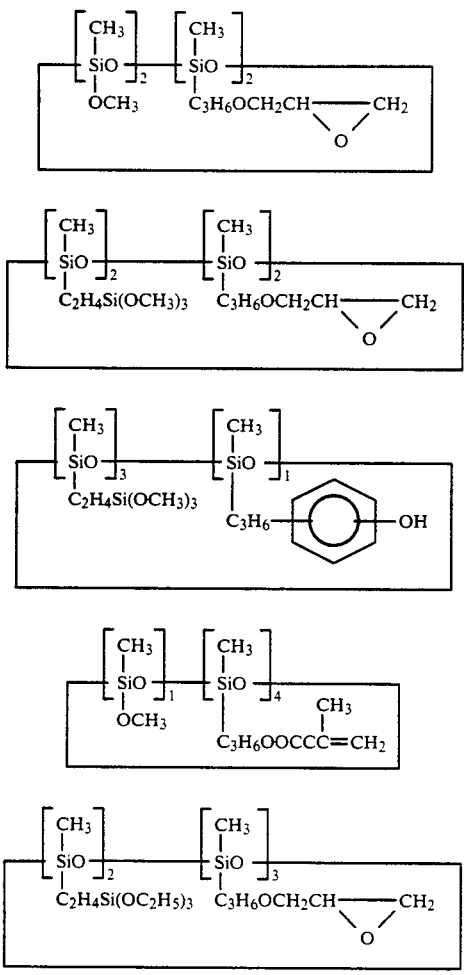

The organocyclosiloxane according to the present invention is readily prepared by the reaction of (A) an organohydrogencyclosiloxane, (B) an organic functional compound and (C) an alcohol or alkoxysilyl-containing unsaturated hydrocarbon in the presence of (D) a hydrosilylation-reaction catalyst.

The organohydrogencyclosiloxane comprising component (A) is the principal starting material for the organocyclosiloxane according to the present invention, and the former is expressed by the following general formula.

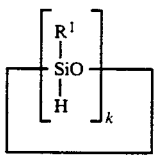

In the preceding formula, the group $R^1$ has its previously defined meaning and k corresponds to the number of organohydrogensiloxane repeat units, k being an integer with a value in the range of 3 to 8. This range is specified for the value of k because the organohydrogencyclosiloxane cannot exist when k is less than 3, while the industrial synthesis of the organohydrogencyclosiloxane becomes problematic when k exceeds 8.

The organohydrogencyclosiloxane under consideration is concretely exemplified by 1,3,5,7-tetramethylcyclotetrasiloxane and 1,3,5,7,9-pentamethylcyclopentasiloxane.

Component (B) is an organic compound which is selected from the glycidoxyalkenes, methacryloxyalkenes, N-(trialkylsilyl)aminoalkenes, (hydroxyphenyl)alkenes, and haloalkenes. Concrete examples of this component are as follows: glycidoxyvinyl and glycidoxyallyl for the glycidoxyalkenes; methacryloxyvinyl and methacryloxyallyl for the methacryloxyalkenes; N-(trimethylsilyl)aminoallyl and N-(triethylsilyl)aminoallyl for the N-(trialkylsilyl)aminoalkenes; o-(hydroxyphenyl)allyl and p-(hydroxyphenyl)allyl for the (hydroxyphenyl)alkenes; and 3-chloroallyl for the haloalkenes. The organocyclosiloxane according to the present invention is produced by the reaction of the silicon-bonded hydrogen atoms in component (A) with this organic compound comprising component (B) as well as with component (C) (alcohol or alkoxysilyl-containing unsaturated hydrocarbon) in the presence of catalyst (D). At least 1 mole of component (B) should be added in the preparative method according to the present invention per 1 mole of component (A). The yield of organocyclosiloxane according to the present invention is substantially reduced when less than 1 mole of component (B) is used per mole of component (A).

Component (C) comprises alcohols and alkoxysilyl-containing unsaturated hydrocarbons, and this component is concretely exemplified by methanol and ethanol for the alcohols and vinyltrimethoxysilane, allyltrimethoxysilane, methylvinyldimethoxysilane, vinyltriethoxysilane, and allyltriethoxysilane for the alkoxysilyl-containing unsaturated hydrocarbons. The organocyclosiloxane according to the present invention is synthesized by the reaction of the silicon-bonded hydrogen atoms in component (A) with the alcohol or alkoxysilyl-containing unsaturated hydrocarbon comprising component (C) as well as with component (B) in the presence of component (D). At least 1 mole of component (C) should be added in the preparative method according to the present invention per 1 mole of component (A). The yield of organocyclosiloxane according to the present invention is substantially reduced when less than 1 mole of component (C) is used per mole of component (A).

The hydrosilylation-reaction catalyst comprising component (D) functions as a catalyst for the reaction between the silicon-bonded hydrogen atoms on component (A) with components (B) and (C). While component (D) may take the form of any hydrosilylation-reaction catalyst in general use, platinum-type catalysts are particularly preferred. Said platinum-type catalysts are exemplified by platinum black, platinum-on-carbon, chloroplatinic acid, alcohol solutions of chloroplatinic acid, chloroplatinic acid/olefin complexes, and chloroplatinic acid/vinylsiloxane complexes. Component (D) should be added in the invention's preparative method in a generally employed catalytic quantity. When component (D) takes the form of a platinum-type catalyst, it is preferably used within the range of 10 to 1,000 ppm as platinum metal atoms referred to the total weight of components (A) plus (B) plus (C).

The reaction temperature is not specifically restricted for the preparative method according to the present invention, but temperatures in the range of 40 to 100 degrees Centigrade are generally preferred. When the reaction temperature falls below 40 degrees Centigrade, the yield of organocyclosiloxane according to the present invention (i.e., wherein each molecule contains both Si-bonded alkoxy and organofunctional groups) is reduced. This is a consequence of a selective reaction of component (B) with component (A), which occurs because the component (A)+component (B) reaction rate is faster than the component (A)+component (C) reaction rate at these temperatures. Secondary reactions tend to occur when the reaction temperature exceeds 100 degrees Centigrade.

The preparative method according to the present invention may be executed in a solventless system or an organic solvent may be employed. No particular restriction is placed on organic solvents which may be employed by the present invention, but nonpolar organic solvents such as toluene and xylene are preferred.

The molecular structure of the organocyclosiloxane according to the present invention can be determined by various analytical methods. Thus, for example, the functional groups in the organocyclosiloxane according to the present invention can be determined by nuclear magnetic resonance spectral analysis, infrared absorption spectral analysis, or ultraviolet absorption spectral analysis.

Because each molecule contains Si-bonded alkoxy and organofunctional groups, the organocyclosiloxane according to the present invention is an effective silane coupling agent. The corresponding surface properties, mechanical properties, and electrical properties are improved through its application to the surface of glass fiber or inorganics or through its addition to various types of plastics according to methods well known in the art.

EXAMPLES

The present invention will be explained in greater detail through the following illustrative examples.

EXAMPLE 1

Two hundred and forty grams of 1,3,5,7-tetramethyl-cyclotetrasiloxane (approximately 1 mole) and 0.01 g of chloroplatinic acid were introduced with mixing into a stirrer-equipped 1 liter roundbottom flask. This was followed by heating to 50 degrees Centigrade. A liquid mixture consisting of 239 g of allyl glycidyl ether (approximately 2 moles) and 310 g of vinyltrimethoxysilane (approximately 2 moles) was added dropwise from an addition funnel over a period of 4 hours. The temperature of the reaction solution during this interval was 50 to 80 degrees Centigrade. The reaction solution was then heated to 80 to 100 degrees Centigrade and stirred for an additional 1 hour. The reaction solution was then brought to 20 mmHg/80 degrees Centigrade and stripped for 1 hour in order to remove unreacted starting material. Stripping afforded 710 g of a product in the form of a light yellow, transparent liquid.

The obtained product was submitted to infrared absorption spectroscopic analysis and nuclear magnetic resonance spectroscopic analysis, and the results confirmed the product to be an organocyclosiloxane with the following general formula

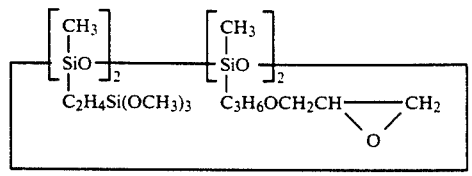

EXAMPLE 2

Two hundred and forty grams of 1,3,5,7-tetramethyl-cyclotetrasiloxane (approximately 1 mole) and 0.01 g chloroplatinic acid were introduced with mixing into a stirrer-equipped 1 liter roundbottom flask. This was followed by heating to 50 degrees Centigrade. A liquid mixture consisting of 279 g of 2-allylphenol (approximately 2 moles) and 310 g of vinyltrimethoxysilane (approximately 2 moles) was added dropwise from an addition funnel over a period of 4 hours. The temperature of the reaction solution during this interval was 50 to 80 degrees Centigrade. The reaction solution was then heated to 80 to 100 degrees Centigrade and stirred for an additional 1 hour. The reaction solution was then brought to 50 mmHg/110 degrees Centigrade and stripped for 1 hour in order to remove unreacted starting material. Stripping afforded 740 g of a product in the form of a light yellow, transparent liquid.

The obtained product was submitted to infrared absorption spectroscopic analysis and nuclear magnetic resonance spectroscopic analysis, and the results confirmed the product to be an organocyclosiloxane with the following general formula

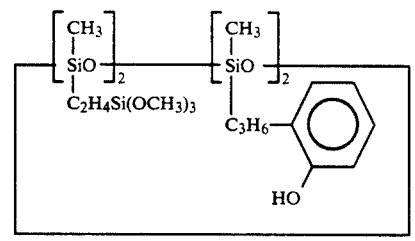

We claim:

1. An organocyclosiloxane having the general formula

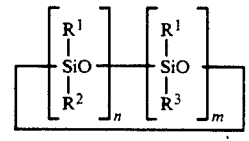

wherein $R^1$ is independently selected from the group consisting of a monovalent hydrocarbon group having 1 to 8 carbon atoms and a monovalent halogen-substituted hydrocarbon group having 1 to 8 carbon atoms, $R^2$ is selected from the group consisting of an alkoxy group and an alkoxysilylalkyl group, $R^3$ is an organofunctional group selected from the group consisting of glycidoxyalkyl groups, methacryloxyalkyl groups, N-(trialkylsilyl)aminoalkyl groups, (hydroxyphenyl)alkyl groups, and haloalkyl groups and n and m each represent an integer having a value of 1 to 6 with the proviso that n+m is an integer with a value of 3 to 8.

2. The organocyclosiloxane according to claim 1, wherein $R^2$ is selected from the group consisting of methoxy, ethoxy, (trimethoxysilyl)ethyl, (trimethoxysilyl)propyl, (methyldimethoxysilyl)ethyl, (triethoxysilyl)ethyl, (triethoxysilyl)propyl and (diethoxymethylsilyl)ethyl.

3. The organocyclosiloxane according to claim 2, wherein $R^3$ is selected from the group consisting of glycidoxyethyl, glycidoxypropyl, methacryloxyethyl, methacryloxypropyl, N-(trimethylsilyl)aminopropyl, N-(triethylsilyl)aminopropyl, o-(hydroxyphenyl)propyl, m-(hydroxyphenyl)propyl, p-(hydroxyphenyl)propyl, chloropropyl and chlorobutyl.

4. The organocyclosiloxane according to claim 3, wherein $R^1$ is selected from the group consisting of alkyl radicals having 1 to 8 carbon atoms, phenyl, chloromethyl and 3,3,3-trifluoropropyl.

5. The organocyclosiloxane according to claim 4, wherein $R^1$ is a methyl radical.

6. The organocyclosiloxane according to claim 5, wherein $R^2$ is selected from the group consisting of methoxy, (trimethoxysilyl)ethyl and (trimethoxysilyl)propyl radicals.

7. The organocyclosiloxane according to claim 6, wherein $R^3$ is selected from the group consisting of glycidoxypropyl, methacryloxypropyl and N-(trimethylsilyl)aminopropyl.

* * * * *